(12) United States Patent
Farber

(10) Patent No.: US 10,451,582 B1
(45) Date of Patent: Oct. 22, 2019

(54) PLANAR LAMBDA SENSOR DESIGN TO BE USED WITH PULSE DISCHARGE TECHNIQUE FOR CONCURRENT $NO_x/NH_3$ MEASUREMENTS

(71) Applicant: BJR Sensors, LLC, Solon, OH (US)

(72) Inventor: Boris Farber, Solon, OH (US)

(73) Assignee: BJR Sensors LLC, Solon, OH (US)

( * ) Notice: Subject to any disclaimer, the term of this patent is extended or adjusted under 35 U.S.C. 154(b) by 22 days.

(21) Appl. No.: 15/530,498

(22) Filed: Jan. 23, 2017

(51) Int. Cl.
*G01N 27/407* (2006.01)
*G01N 27/416* (2006.01)

(52) U.S. Cl.
CPC ..... *G01N 27/4071* (2013.01); *G01N 27/4074* (2013.01); *G01N 27/4163* (2013.01)

(58) Field of Classification Search
CPC .............. G01N 27/407; G01N 27/4071–4075
See application file for complete search history.

(56) References Cited

U.S. PATENT DOCUMENTS

| 5,619,433 | A | * | 4/1997 | Wang | G05B 17/02 703/18 |
| 2002/0038763 | A1 | * | 4/2002 | E | C23C 18/08 204/427 |
| 2005/0284772 | A1 | * | 12/2005 | Farber | G01N 27/4065 205/775 |
| 2015/0013431 | A1 | * | 1/2015 | Kakimoto | G01N 27/419 73/23.31 |

* cited by examiner

*Primary Examiner* — Alexander S Noguerola
(74) *Attorney, Agent, or Firm* — John D. Gugliotta

(57) ABSTRACT

A gas sensor is provided in which a solid electrolyte tape of yttria doped zirconia is layered with tapes of alumina and a tape if mixed alumina-zirconia. This zirconia layer has structural modifications to increase $NO_x$ and $NH_3$ sensitivity which the capacitance is significantly increased by creating a composite layer of platinum (Pt) plus a layer of yttrium-stabilized-zirconia (YSZ) with Pt fraction of approximately between around 10% by volume to around 25% by volume. A 100-200 µm thick mixed tape layer of porous $MgAl_2O_4$ is provided on top of the alumina-zirconia layer. Under the alumina-zirconia tape is an exhaust gas sensing electrode which connects to a contact pad through the lead. A reference electrode, which connects to the pad through a lead, is disposed in fluid communication with a reference chamber. Proximate alumina tapes and a heater are connected to the contact pad, which is connected to corresponding leads.

14 Claims, 6 Drawing Sheets

PLANAR LAMBDA SENSOR DESIGN TO BE USED WITH PULSE DISCHARGE TECHNIQUE FOR CONCURRENT $NO_x/NH_3$ MEASUREMENTS

BACKGROUND OF THE INVENTION

1. Field of the Invention

The present invention relates to a improvements in planar style lambda gas sensors and, more particularly, to method of making, configuring, using and improving such sensors to allow for concurrent use in measurements of both $NO_x$ and $NH_3$ levels.

2. Description of the Related Art

The Pulse Discharge Technique has been shown and described in combination with zirconia based lambda sensor in various Related Applications in order to improve sensitivity to an analyzed gas. Generally, sensitivity to an analyzed gas is determined by the sensor capacitance—capacity to retain charge for sufficiently long time under conditions of the Pulse Discharge Technique (hereinafter, "PDT") for detection of gas reactions with charge carriers on the electrode surface during the pauses between the charging pulses.

A typical design of a commercially available planar-type lambda sensor structure according to the PRIOR ART is shown in FIG. 1 and described more fully in U.S. Pat. No. 6,800,158, issued in the name of Polikarpus et al and assigned to Delphi Technology, Inc. For this arrangement, a solid electrolyte tape 1 is Yttria doped Zirconia, tapes 2 are alumina, and tape 3 is an alumina-Zirconia mixed tape which provides particulate protection. Under tape 3 is the exhaust gas sensing electrode 4 which connects to the contact pad 5 through the lead 6, While the reference electrode 7, Which connects to the pad 8 through lead 9, is disposed in fluid communication With reference chamber 10. Proximate alumina tapes 2, heater 11 is connected to contact pad 13, which is connected to corresponding leads 14 and 16.

Due to relatively small surface areas of the exhaust gas sensing and reference Pt electrodes, an initial capacitance of such a described structure is relatively small. This results in a low sensitivity to NO under conditions of the PDT. And, because of such low sensitivity, such sensor configurations as currently disclosed and manufactured demonstrate no measurable response to $NO_x$.

Consequently, a need exists for improving the sensitivity of such prior art planar sensors for measurements of $NO_x$ and/or $NH_3$.

SUMMARY OF THE INVENTION

It is thus an object of the present invention to provide an improved planar style lambda gas sensors.

Primary features of the present invention include providing a method of making, configuring, using and improving such planar style lambda gas sensors to allow for concurrent use in measurements of both $NO_x$ and $NH_3$ levels.

Briefly described according to a preferred embodiment of the present invention, the general utilization of the PDT is improved and adapted for use during charging a sensor during positive and negative voltage pulses, with the subsequent measuring of sensor discharge rate during the pauses following charging voltage pulses. Such a treatment allows the relatively small surface areas of the exhaust gas sensing and reference platinum (Pt) electrodes to have increased sensitivity to $NO_x$. With such increased sensitivity, such sensor configurations can be manufactured to demonstrate an $NO_x$ response. With proper calibration, differentials in the rate of charge and discharge at various temperatures can further be measured in order to provide a sensor that may be used for both $NO_x$ measurement as well as $NH_3$ measurement within a same combined gas stream.

It is an advantage of the present invention to provide a gas sensor for use in combustion exhaust.

Yet another advantage of the present invention to provide an improved planar type gas sensor that is capable of measuring $NO_x$ concentrations.

It is yet another advantage of the present invention to provide an improved planar type gas sensor that is capable of measuring $NH_3$ concentrations in a mixed gas stream that includes $NO_x$.

Further features of the invention will become apparent in the course of the following description.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

DESCRIPTION OF THE PREFERRED EMBODIMENTS

The best mode for carrying out the invention is presented in terms of its preferred embodiment, herein depicted within the Figures. It should be understood that the legal scope of the description is defined by the words of the claims set forth at the end of this patent and that the detailed description is to be construed as exemplary only and does not describe every possible embodiment since describing every possible embodiment would be impractical, if not impossible. Numerous alternative embodiments could be implemented, using either current technology or technology developed after the filing date of this patent, which would still fall within the scope of the claims.

It should also be understood that, unless a term is expressly defined in this patent there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term by limited, by implication or otherwise, to that single meaning. Finally, unless a claim element is defined by reciting the word "means" and a function without the recital of any structure, it is not intended that the scope of any claim element be interpreted based on the application of 35 U.S.C. § 112(f).

The best mode for carrying out the invention is presented in terms of its preferred embodiment, herein depicted within the Figures.

1. DETAILED DESCRIPTION OF THE FIGURES

Figure 1:
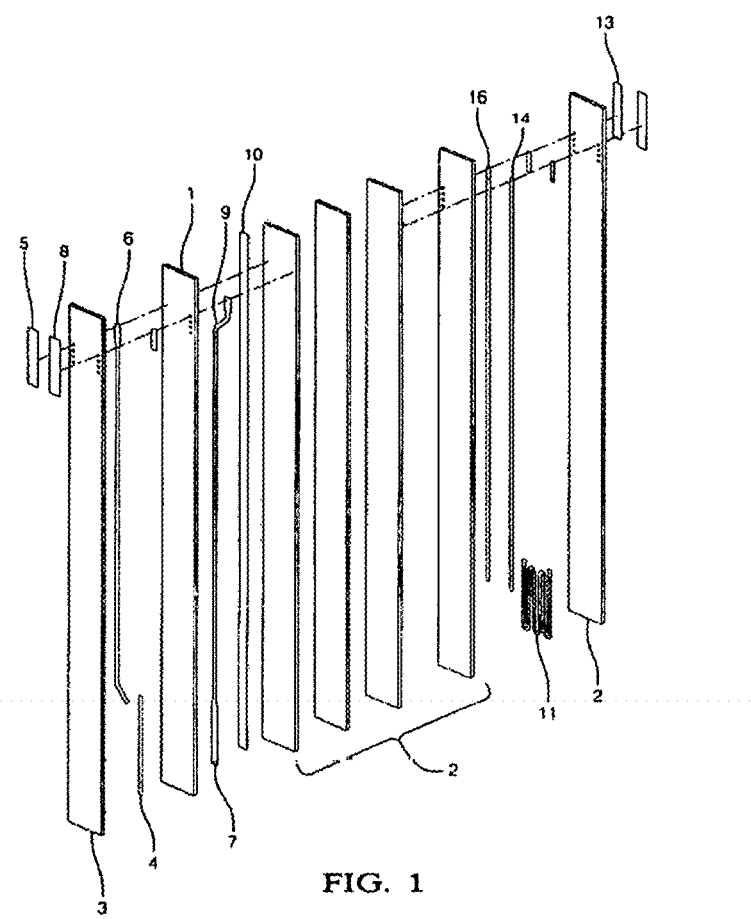
FIG. 1 depicts an exploded perspective view of a planar style lambda type sensor according to the PRIOR ART.
Figure 2:
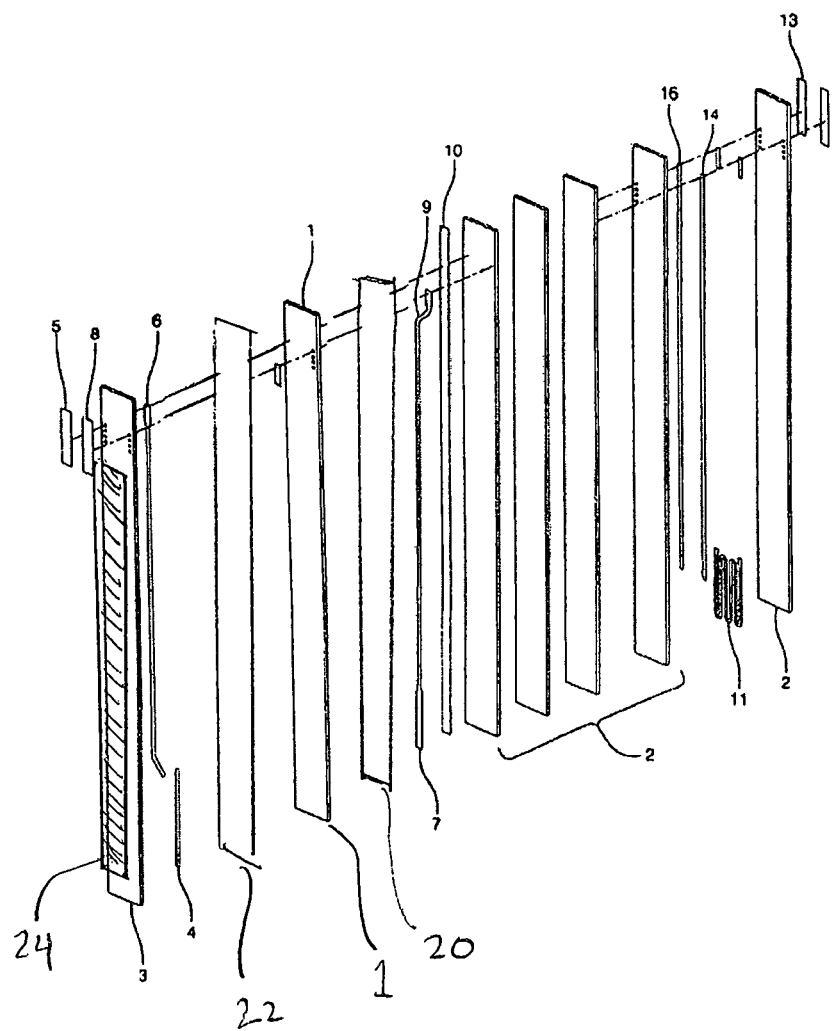
FIG. 2 depicts an exploded perspective view of an improved planar style type lambda sensor according to the preferred embodiment of the present invention.

A preferred embodiment of the present invention provides an improvement of a sensor of the PRIOR ART as shown in FIG. 1, and provides an improved sensor as shown in FIG. 2 through both structural modifications as well as electrode surface activation. For exemplary and preferred structural modifications to increase $NO_x$ and $NH_3$ sensitivity, the capacitance of a composite stabilized Zirconia/Pt structure may be significantly increased by creating a composite layer of Platinum (Pt) plus a layer of yittrium-stabilized-zirconia with a Pt fraction of approximately between around 10% by volume to around 25% by volume. This intermediate YSZ-Pt composite layer is provided between the electrolyte and the electrodes (reference numeral 20 between layer 4 and layer 1; and, reference numeral 22 between layer 1 and layer 7 in FIG. 2). It is preferred that the thickness of the composite layer be between approximately 10μ to approximately 20μ. As should be apparent to a person having ordinary skill in the relative art, in light of the present teachings, such a composite layer may be applied by thick film technologies such as, for example, as a paste of YSZ with dispersed Pt particles.

Further structural modifications that may be incorporated include making use of the demonstrated catalytic properties of $MgAl_2O_4$ for $NO_x$ reduction. (See, for example, Coillard, Debeda et al. 2001[1]). To eliminate differential responses to NO and $NO_2$ a layer of porous $MgAl_2O_4$ on top of layer 3 is applied. Such a porous layer 24 is preferably between around 100 μm thick to around 200 μm thick. Such a layer within this preferred range eliminates differential responses to NO and $NO_2$, and additionally serves as erosion and water droplet protection.

[1]. Collard, V., H. Debeda, C. Lucat and F. Meni (2001). "Nitrogen monoxide detection with a planar spinel coated amperometic sensor." Sensors and Actuators B—Chemical 78

For exemplary and preferred electrode surface activation, an increase in the active electrode area is achieved. The Pt electrode activation is achieved by treatment in a strongly reducing atmosphere (such as, for example, 5% H2 with a balance N2) at a temperature T=1000° C., Dew point <−45° C. It has been found that such as surface activation treatment may be used following the protocol as taught in the Related Applications, and specifically that of U.S. Pat. No. 8,110,080. As therein generally described, the subsequent measuring of sensor discharge rate during the pauses following charging voltage pulses allows the relatively small surface areas of the exhaust gas sensing and reference Pt electrodes to have increased sensitivity to $NO_x$. With such increased sensitivity, such sensor configurations can be manufactured to demonstrate an $NO_x$ response. With proper calibration, differentials in the rate of charge and discharge at various temperatures can further be measured in order to provide a sensor that may be used for both $NO_x$ measurement as well as $NH_3$ measurement within a same combined gas stream.

Figure 3:
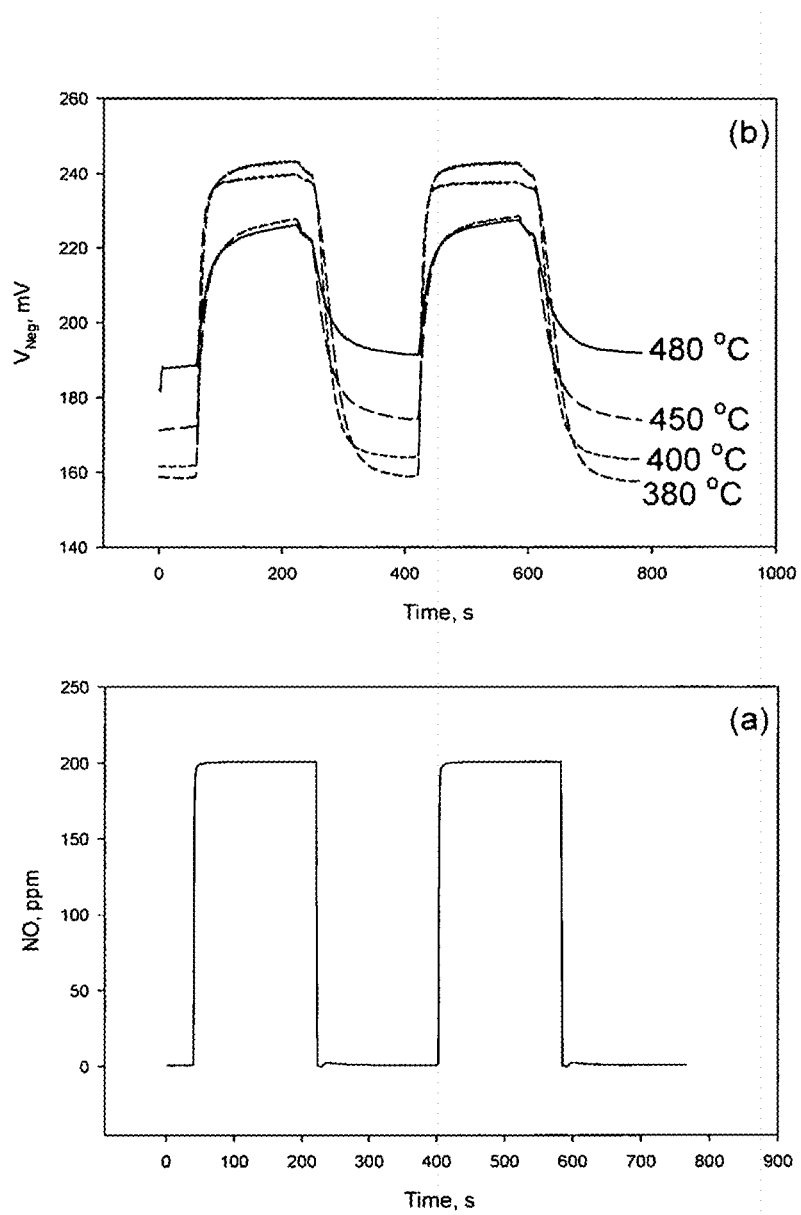
FIG. 3 is a graph showing $V_{Neg}$ response of a planar commercial lambda sensor to injection of NO (0-200 ppm) at different sensor operating temperatures.
Figure 4:
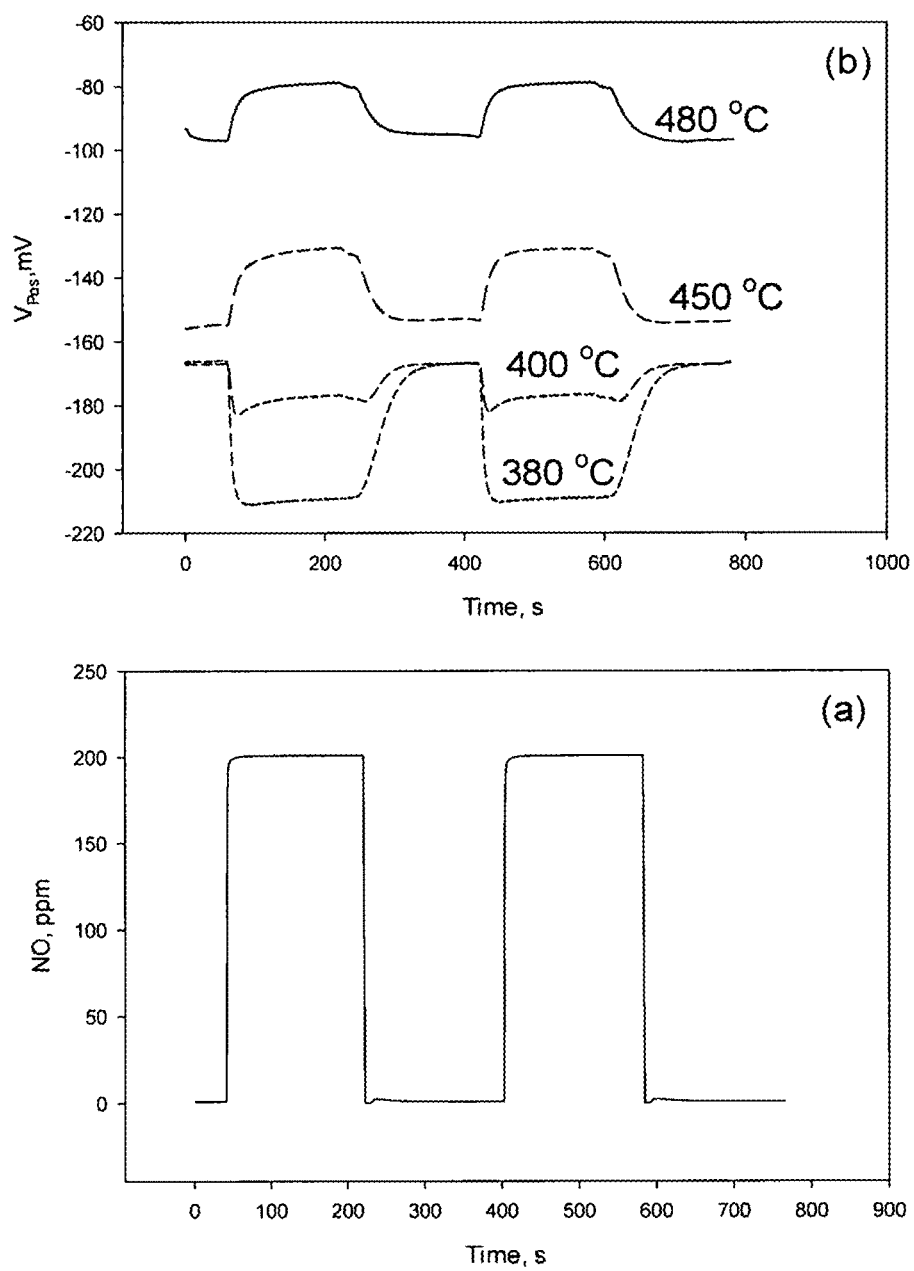
FIG. 4 is a graph showing $V_{Pos}$ response of a planar commercial lambda sensor to injection of NO (0-200 ppm) at different sensor operating temperatures.

Combined $NO_x$ and $NH_3$ sensitivity is enabled through the proper sensor operating temperature selection for concurrent measurements of $NO_x$ and $NH_3$. Sensor responses to the pulses of NO at 0-200 ppm is shown in FIG. 3 ($V_{Neg}$) and FIG. 4 ($V_{Pos}$) at different sensor operating temperatures in the range of 380–480° C. Reaction of the sensor responses to the injection of NO in the analyzed gas is different for $V_{Neg}$ and $V_{pos}$. As shown, $V_{Neg}$ increase with the increase in the NO concentration (see FIG. 2). $V_{Pos}$ values increase by absolute value at T<=400° C., but decreasing by absolute amplitude at higher temperatures T>400° C.

Figure 5:
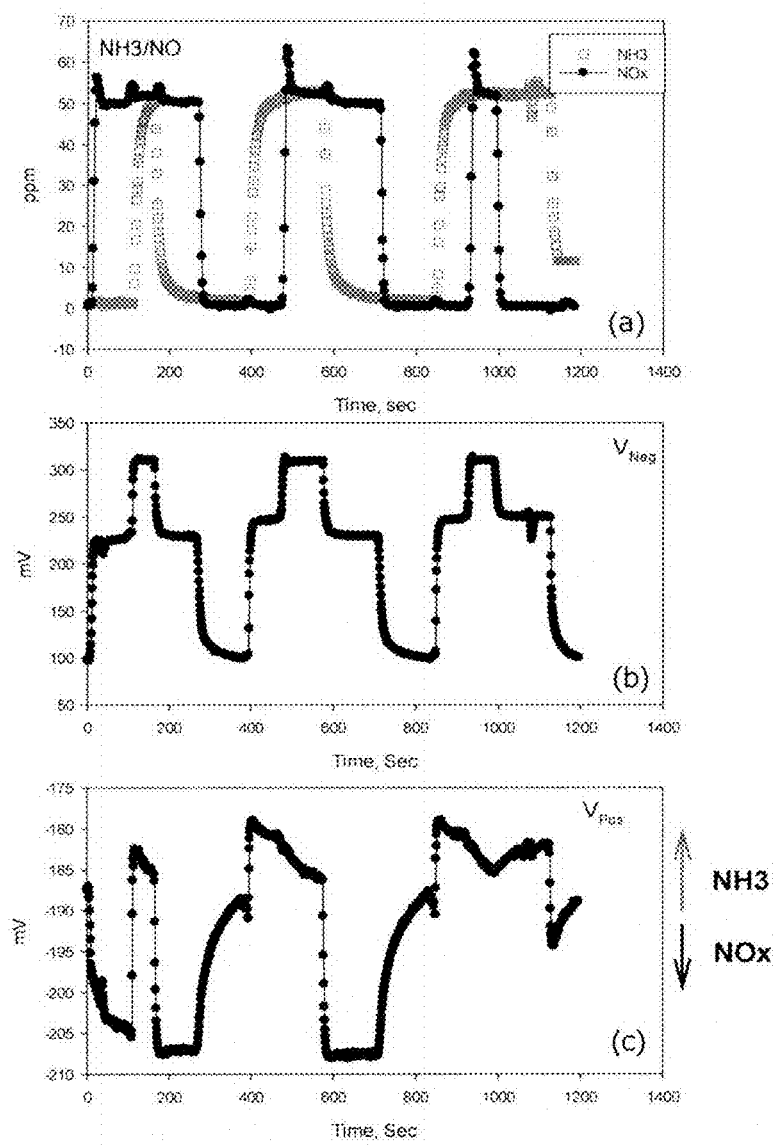
FIG. 5 depicts the response of a thimble-type lambda sensor to combined presence of NO and $NH_3$ at the sensor operating temperature of 350° C.

Reaction of the sensor responses to the presence of NO and $NH_3$ in the analyzed gas was established for a thimble-type lambda sensors, and the results depicted in FIG. 5. This method corresponds with the teachings of the Related Applications generally, and U.S. Pat. No. 8,110,080 in particular (and incorporated by reference herein as if full rewritten). In response to NO injection, both $V_{Neg}$ and $V_{pos}$ values increase by absolute values. The presence of $NH_3$ increases $V_{Neg}$ value, but decreases $V_{Pos}$ values. Consequently, sensitivity of $V_{Pos}$ values to the presence of $NH_3$ is stronger than to the presence of $NO_x$.

Figure 6:
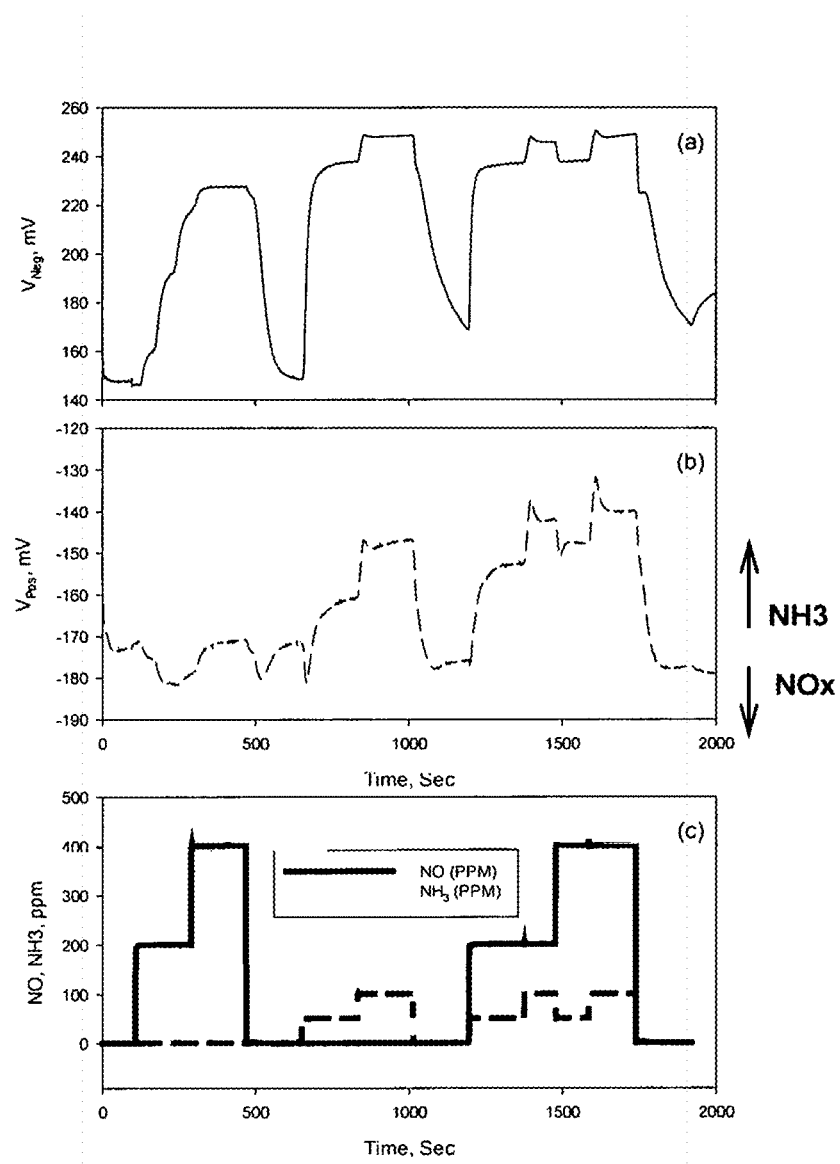
FIG. 6 depicts the response of a planar-type commercial lambda sensor to combined presence of NO and $NH_3$ at the sensor operating temperature of 400° C.

Similar responses to the presence of $NO_x$ and $NH_3$ were detected for a planar commercial lambda sensor operating at T=400° C. as shown in FIG. 6.

2. OPERATION OF THE PREFERRED EMBODIMENT

In operation, the present invention provide an improved planar style lambda gas sensor that allows for concurrent use in measurements of both $NO_x$ and $NH_3$ levels. The general utilization of the PDT is improved and adapted for use during charging a sensor during positive and negative voltage pulses, with the subsequent measuring of sensor discharge rate during the pauses following charging voltage pulses. Such a treatment allows the relatively small surface areas of the exhaust gas sensing and reference Pt electrodes to have increased sensitivity to $NO_x$. With such increased sensitivity, such sensor configurations can be manufactured to demonstrate an $NO_x$ response as well as $NH_3$ measurement within a same combined gas stream.

Such a gas sensor configuration and operation is particularly commercially useful for use in measuring vehicle combustion exhaust $NO_x/NH_3$ concentrations. To find optimum operational conditions for concurrent measurements of $_{NOx}$ and $_{NH3}$, measuring sensor responses as $V_{Neg}$ and $V_{pos}$ at different operating temperatures is accomplished and the operating temperature selected that results in increases in $V_{Neg}$ and $V_{pos}$ by absolute values in response to $NO_x$ injection in the analyzed gas stream.

The foregoing descriptions of specific embodiments of the present invention are presented for purposes of illustration and description. They are not intended to be exhaustive nor to limit the invention to precise forms disclosed and, obviously, many modifications and variations are possible in light of the above teaching. The embodiments are chosen and described in order to best explain principles of the invention and its practical application, to thereby enable others skilled in the art to best utilize the invention and its various embodiments with various modifications as are suited to the particular use contemplated. It is intended that a scope of the invention be defined broadly by the Drawings and Specification appended hereto and to their equivalents. Therefore, the scope of the invention is in no way to be limited only by any adverse inference under the rulings of *Warner-Jenkinson Company, v. Hilton Davis Chemical*, 520 US 17 (1997) or *Festo Corp. v. Shoketsu Kinzoku Kogyo Kabushiki Co.*, 535 U.S. 722 (2002), or other similar case-law or subsequent precedent should not be made if any future claims are added or amended subsequent to this Patent Application.

What is claimed is:

1. A gas sensor comprising:
   a solid electrolyte layer of yttria stabilized zirconia (YSZ) sandwiched between exhaust gas sensing electrodes and reference electrodes and layered with layers of alumina and a layer of mixed alumina-zirconia;
   an additional $NO_x$ and $NH_3$ sensitive composite layer of Pt and YSZ having a Pt fraction of approximately between around 10% by volume to around 25% by volume and sandwiched between the layer of YSZ and electrodes;
   a mixed layer of porous $MgAl_2O_4$ provided on top of the alumina-zirconia layer and covering a measurement portion exposed to analyzed gas of the gas sensing electrode;
   an exhaust gas sensing electrode under the alumina-zirconia layer which connects to a contact pad through a lead; and
   a reference electrode connecting to the pad through a lead and disposed in fluid communication with a reference chamber.

2. The gas sensor of claim 1, wherein said mixed layer of porous $MgAl_2O_4$ is between approximately 100 mm thick to approximately 200 mm thick.

3. The gas sensor of claim 1, further comprising a composite YSZ-Pt layer.

4. The gas sensor of claim 3, wherein said YSZ-Pt layer has a Pt content of between approximately 10 vol % to approximately 25 vol %.

5. In the gas sensor of claim 1, wherein a composite YSZ-Pt layer is provided between an electrolyte and an electrode.

6. In the gas sensor of claim 5, wherein said YSZ-Pt layer has a Pt content between approximately 10 vol % and approximately 25 vol %.

7. In the gas sensor of claim 6, wherein said composite layer of Pt and YSZ has a thickness between approximately 10 µm to approximately 20 µm.

8. In the gas sensor of claim 7, wherein said composite layer of Pt and YSZ comprises a paste of YSZ with dispersed Pt particles.

9. The gas sensor of claim 1 wherein increased sensor sensitivity to $NO_x$ and $NH_3$ is created via increasing electrode active surface area by activation of the exhaust gas sensing electrodes and the reference electrodes with a treatment in a strongly reducing atmosphere of 5% H2 balance N2.

10. The gas sensor of claim 9, wherein said treatment temperature is T=1000° C. and the treatment Dew point is <−45° C.

11. A gas sensor, wherein the improvement comprises:
    increasing sensor capacitance by treatment with a pulse discharge technique for providing sensitivity for concurrent $NO_x$ and $NH_3$ measurements; and
    wherein the gas sensor comprises a mixed layer of porous $MgAl_2O_4$ on top of an alumina-zirconia layer in order to eliminate differential response to NO and $NO_2$.

12. In the gas sensor of claim 11, wherein said $MgAl_2O_4$ porous layer is between approximately 100 mm to approximately 200 mm thick.

13. The gas sensor of claim 11, wherein increased sensor sensitivity to $NO_x$ and $NH_3$ is created via increasing electrode active surface area by activation of the exhaust gas sensing electrodes and the reference electrodes with a treatment in a strongly reducing atmosphere of 5% H2 balance N2.

14. The gas sensor of claim 13, wherein said treatment temperature T=1000° C. and the treatment Dew point is <−45° C.

* * * * *